(12) United States Patent
Scholz

(10) Patent No.: US 11,260,152 B2
(45) Date of Patent: Mar. 1, 2022

(54) APPARATUS FOR COLLECTING BREAST MILK

(71) Applicant: Melanie Scholz, Kitchener (CA)

(72) Inventor: Melanie Scholz, Kitchener (CA)

(73) Assignee: KindestCup.com, Kitchener (CA)

( * ) Notice: Subject to any disclaimer, the term of this patent is extended or adjusted under 35 U.S.C. 154(b) by 208 days.

(21) Appl. No.: 16/414,980

(22) Filed: May 17, 2019

(65) Prior Publication Data

US 2019/0351114 A1 Nov. 21, 2019

Related U.S. Application Data

(60) Provisional application No. 62/672,970, filed on May 17, 2018.

(51) Int. Cl.
*A61M 1/06* (2006.01)
(52) U.S. Cl.
CPC ............ *A61M 1/064* (2014.02); *A61M 1/068* (2014.02); *A61M 2205/3337* (2013.01)
(58) Field of Classification Search
CPC ........ A61M 1/064; A61M 1/06; A61M 1/068; A61M 2205/3337; A61M 2205/071; A61M 1/066; A61M 1/062; A61M 2205/583; A61J 13/00; A61J 9/00
See application file for complete search history.

(56) References Cited

U.S. PATENT DOCUMENTS

| 2,748,771 | A | * | 6/1956 | Richards | A61F 13/141 604/346 |
| 7,662,018 | B1 | * | 2/2010 | Thompson | A61J 13/00 450/37 |
| 8,118,772 | B2 | * | 2/2012 | Dao | A61M 1/06 604/74 |
| 9,498,565 | B2 | | 11/2016 | Nowroozi et al. | |

FOREIGN PATENT DOCUMENTS

WO WO-2004000390 A1 * 12/2003 .......... A61M 1/0068

* cited by examiner

*Primary Examiner* — Amber R Stiles
(74) *Attorney, Agent, or Firm* — Bereskin & Parr LLP

(57) ABSTRACT

Apparatuses for collecting breast milk are described herein. The apparatuses include a body having a front side and a rear side opposed to the front side, the body defining a cavity and the rear side defining an opening shaped for receiving a portion of a user's breast. The cavity has an upper region for receiving the portion of the user's breast and a lower region for collecting the breast milk. The opening is positioned adjacent to the upper region of the cavity. The apparatuses may include a suction generating device for modulating the negative pressure in the cavity when the apparatus is pressed against the user's breast.

15 Claims, 13 Drawing Sheets

APPARATUS FOR COLLECTING BREAST MILK

RELATED APPLICATIONS

This application claims the benefit of U.S. Provisional Patent Application No. 62/672,970, filed May 17, 2018, and the entire contents of U.S. Provisional Patent Application No. 62/672,970 are hereby incorporated by reference.

BACKGROUND

Breastfeeding is widely encouraged in the first years after birth because of the benefits breast milk provides to infants. Specifically, breast milk is known to provide nutrients and immunities required for growth and development. Studies have also shown that breastfeeding promotes health of mothers.

Although breastfeeding has these advantages, it also has limitations. For instance, mothers often need to be away from their infant during feeding times. Additionally, mothers may get uncomfortable when breast milk is not removed (i.e. baby is not hungry or sleeping). During such situations, breastfeeding may become difficult or even unmanageable.

Breast pumps offer mothers an opportunity to extract breast milk and store it for later use. Although conventional breast pumps provide suction, they typically are not as effective at expressing breast milk as natural breastfeeding and as hand expression. Alveoli in the breast tissue generate and hold breast milk shortly after a mother gives birth. To draw this milk out of the alveoli and through the milk ducts, breast pumps generate suction directed towards the nipple. In response, milk is drawn from the alveoli via milk ducts through pores in the nipple. In contrast, during hand expression pressure is exerted directly to the alveoli. The action of the hands stimulates active milk ejection by activating myoepithelial cells surrounding the alveoli and milk ducts that naturally contract and release during breastfeeding. As breast pumps cannot activate the myoepithelial cells surrounding the alveoli and the milk ducts, hand expression more closely resembles natural breast feeding than usage of a breast pump.

Hand expression of breast milk requires a receptacle or container to collect the expressed breast milk for storage. Mothers that currently choose to hand express breast milk typically do so into receptacles that encourage poor posture as the mother typically needs to lean over the receptacle to express the breast milk. Generic receptacles like cups or bowls are generally not able to capture all of the milk expressed from the breast. Expressed breast milk exits the breast from various pores on the nipple and sprays or drips in various directions, often simultaneously. It can be difficult or impossible to direct all of the expressed breast milk into the opening of a generic receptacle. Expressed breast milk that cannot be captured often spills onto clothing or furniture. Furthermore, expressed breast milk that has been captured needs to be transferred into a secondary receptacle for storage or for providing to an infant.

Passive breastfeeding is the loss of breast milk from the breast when the breast releases milk while not breastfeeding, i.e. stimulated by a nursing infant on the other breast or in response to other stimuli such as hearing a baby cry or pleasant touch. Currently, mothers tend not to collect passively expressed breast milk, which can lead to a significant amount of wasted milk.

Cup feeding is a way of administering liquids to an infant without using artificial nipples or teats. Studies have shown that the use of artificial nipples or teats may interfere with the infant's ability to feed at the breast.

Accordingly, there is a need for new or improved apparatuses for collecting hand expressed and passively expressed breast milk and for alternatives to artificial nipples or teats.

SUMMARY

According to a broad aspect, an apparatus for collecting breast milk is described herein. The apparatus includes a body having a front side and a rear side opposed to the front side. The body defines a cavity and the rear side defines an opening shaped for receiving a portion of a user's breast or the breast milk exiting the user's breast. The cavity has an upper region for receiving the portion of the user's breast or the user's breast milk and a lower region for collecting the breast milk. The opening is positioned adjacent to the upper region of the cavity.

In some embodiments, the opening is sized and shaped to conform to the user's breast.

In some embodiments, the opening is sized and shaped to sealingly engage the user's breast.

In some embodiments, the opening is sized and shaped to redirect and capture expressed milk exiting the user's breast from all anatomically possible angles.

In some embodiments, the opening has an upper portion and a lower portion, the upper portion of the opening being narrower than the lower portion.

In some embodiments, the opening is generally triangular shaped having an apex adjacent to a top side of the body.

In some embodiments, the opening is concave.

In some embodiments, a center of the opening is vertically offset from a center of the body.

In some embodiments, a center of the opening is horizontally aligned with a center of the body.

In some embodiments, the apex intersects a seam joining two halves of the body.

In some embodiments, the apex forms a spout for pouring milk out of the cavity.

In some embodiments, the spout is shaped to conform to an infant's mouth or a storage container.

In some embodiments, the apex extends rearwardly from the body to form the spout.

In some embodiments, the apex extends rearwardly from the body relative to the lower portion of the opening to form the spout.

In some embodiments, the cavity is sized to retain a volume of liquid in a range of about 50 mL to 150 mL.

In some embodiments, a lower region of the cavity is sized to retain about 75 mL of breast milk when the body is upright.

In some embodiments, the body is washable.

In some embodiments, the body is sterilizable.

In some embodiments, the body includes a flattened portion a flattened portion to provide for the apparatus to rest on a flat surface without falling over.

In some embodiments, the flattened portion is on one of the top, bottom and front sides of the body.

In some embodiments, the flattened portion is opposed to the opening.

In some embodiments, an inner wall of the cavity is tapered outwardly from a lower region of the body to an upper region.

In some embodiments, the body is translucent.

In some embodiments, the opening is asymmetric.

According to a broad aspect, an apparatus for collecting breast milk is described herein. The apparatus includes a body having a front side and a rear side opposed to the front side. The body defines a cavity and the rear side defines an opening shaped for receiving a portion of a user's breast or the breast milk exiting the user's breast. The cavity has an upper region for receiving the portion of the user's breast or the user's breast milk and a lower region for collecting the breast milk expressed by the user in the upper region of the cavity. The opening is positioned adjacent to the upper region of the cavity. The apparatus also includes a suction generating device coupled to the body to modulate the negative pressure in the cavity to encourage the expression of milk from the user's breast.

In some embodiments, the suction generating device is coupled to the body adjacent to the opening.

In some embodiments, the suction generating device is positioned in an upper portion of the opening.

In some embodiments, the opening has an apex adjacent to a top side of the body and the suction generating device is positioned in the apex of the opening.

BRIEF DESCRIPTION OF THE DRAWINGS

The drawings included herewith are for illustrating various examples of articles, methods, and apparatuses of the present specification. In the drawings.

DETAILED DESCRIPTION

Figure 1:
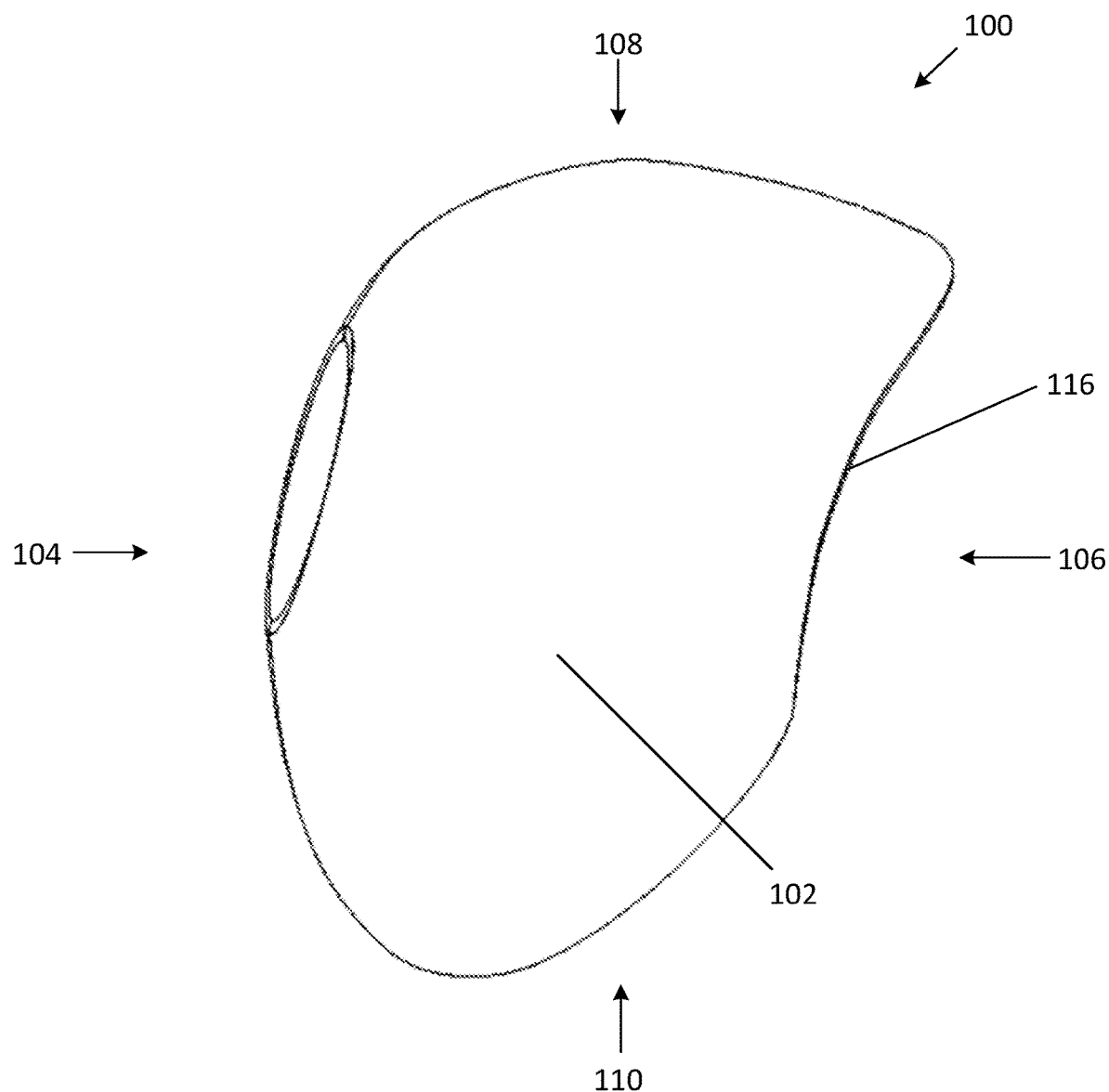
FIG. 1 is a side perspective view of an apparatus for collecting breast milk, according to one embodiment.

Various apparatuses, methods and systems are described below to provide an example of at least one embodiment of the claimed subject matter. No embodiment described below limits any claimed subject matter and any claimed subject matter may cover apparatuses and methods that differ from those described below. The claimed subject matter are not limited to apparatuses, methods and compositions having all of the features of any one apparatus, method or composition described below or to features common to multiple or all of the apparatuses, methods or compositions described below. Subject matter that may be claimed may reside in any combination or sub-combination of the elements or process steps disclosed in any part of this document including its claims and figures. Accordingly, it will be appreciated by a person skilled in the art that an apparatus, system or method disclosed in accordance with the teachings herein may embody any one or more of the features contained herein and that the features may be used in any particular combination or sub-combination that is physically feasible and realizable for its intended purpose.

Furthermore, it is possible that an apparatus, method or system described below is not an embodiment of any claimed subject matter. Any subject matter that is disclosed in an apparatus, method or composition described herein that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

It will also be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

It should be noted that terms of degree such as "substantially", "about" and "approximately" as used herein mean a reasonable amount of deviation of the modified term such that the result is not significantly changed. These terms of degree should be construed as including a deviation of the modified term, such as 1%, 2%, 5%, or 10%, for example, if this deviation would not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made, such as 1%, 2%, 5%, or 10%, for example, if the end result is not significantly changed.

It should also be noted that, as used herein, the wording "and/or" is intended to represent an inclusive—or. That is, "X and/or Y" is intended to mean X or Y or both, for example. As a further example, "X, Y, and/or Z" is intended to mean X or Y or Z or any combination thereof.

In spite of the technologies that have been developed, there remains a need in the field for improvements in the development apparatuses for collecting hand expressed or passively expressed breast milk.

Generally, apparatuses for collecting hand expressed and passively expressed breast milk are described herein. The apparatuses described herein can generally act as a shield to redirect expressed breast milk and can provide a reservoir for collecting expressed breast milk.

In some embodiments, the apparatuses described herein may provide for the collection of hand expressed breast milk and/or the collection of passively expressed breast milk.

Herein, the term "passively expressed" breast milk refers to breast milk that is either expressed from a breast (or leaks from a breast) without the use of a breast pump (e.g. suction) or active manipulation of the breast. For instance, passive expression of breast milk from a second breast naturally occurs when a first breast is actively lactating (e.g. lactating in response to a nursing infant, pumping or hand expression). Further, passive expression of breast milk may occur in response to another stimuli, such as hearing a crying baby or sensitive touch.

In some embodiments, the apparatuses described herein may provide for breast milk collection that is hands-free.

In some embodiments, the apparatuses described herein may provide an adjustable, soft or smooth rim for cup feeding infants directly from the apparatus.

In some embodiments, the apparatuses described herein may provide a tapered reservoir that fills up quickly even when the expressed milk volume is low (positive feedback to the user), and also accommodates larger milk volumes (as described below).

In some embodiments, the apparatuses described herein may include a flattened portion to provide for the apparatus to rest on a flat surface without falling over.

In some embodiments, the apparatuses described herein may be formed from a non-toxic material to inhibit contamination of the contents of the apparatus (e.g. the breast milk).

In some embodiments, the apparatuses described herein may be washable and re-usable.

In some embodiments, the apparatuses described herein may be sized and shaped to comfortably fit in a user's hand.

In some embodiments, the apparatuses described herein may have a capacity of about 75 mL.

In some embodiments, the apparatuses described herein may provide for a user to have an ergonomic upright posture when expressing breast milk.

In some embodiments, the apparatuses described herein may be formed from a transparent or translucent material to provide for the user to see the breast milk accumulating in the apparatus.

In some embodiments, the apparatuses described herein may be soft to the touch for user comfort.

In some embodiments, the apparatuses described herein may be dishwasher safe, sterilizable and freezer-safe (e.g. breast milk therein can be frozen in the apparatus, removed when frozen and stored in a freezer bag).

In some embodiments, the apparatuses described herein may have a spout or a spout-like portion to facilitate pouring the contents of the apparatus (when transferring milk to a milk storage bag, a bottle or any other container or for feeding an infant).

In some embodiments, the apparatuses described herein may interface with a system that can modulate a pressure inside a cavity of the apparatus and apply a negative pressure (i.e. suction) therein when the apparatus is placed against the mother's breast. The negative pressure may be sufficient for the apparatus to releasably couple to the breast by suction and not require the mother to hold the apparatus against the breast as milk is expressed and/or leaks from the breast. In other embodiments, the negative suction may be sufficient to encourage the expression and/or leakage of breast milk from the breast. The negative pressure present inside of the cavity of the apparatus may be modulated manually by the user or another person (i.e. by the user sucking on a portion of the apparatus to remove air from the cavity and modulate a negative pressure therein). In these embodiments, the apparatus may be shaped to conform to the mother's breast to form a seal against the breast when the negative pressure inside of the cavity is modulated. The negative pressure present inside of the cavity of the apparatus may also be modulated by a pump or pump-like device (e.g. a plunger).

Negative pressure in the cavity during expression and/or leaking of breast milk by the mother may provide for collection of passively expressed breast milk. The negative pressure may encourage expression of milk from the breast.

In some embodiments, the negative pressure in the cavity can be sufficient to provide for the apparatus to remain releasably coupled to the user's breast without the user having to hold the apparatus against their breast.

Figure 2:
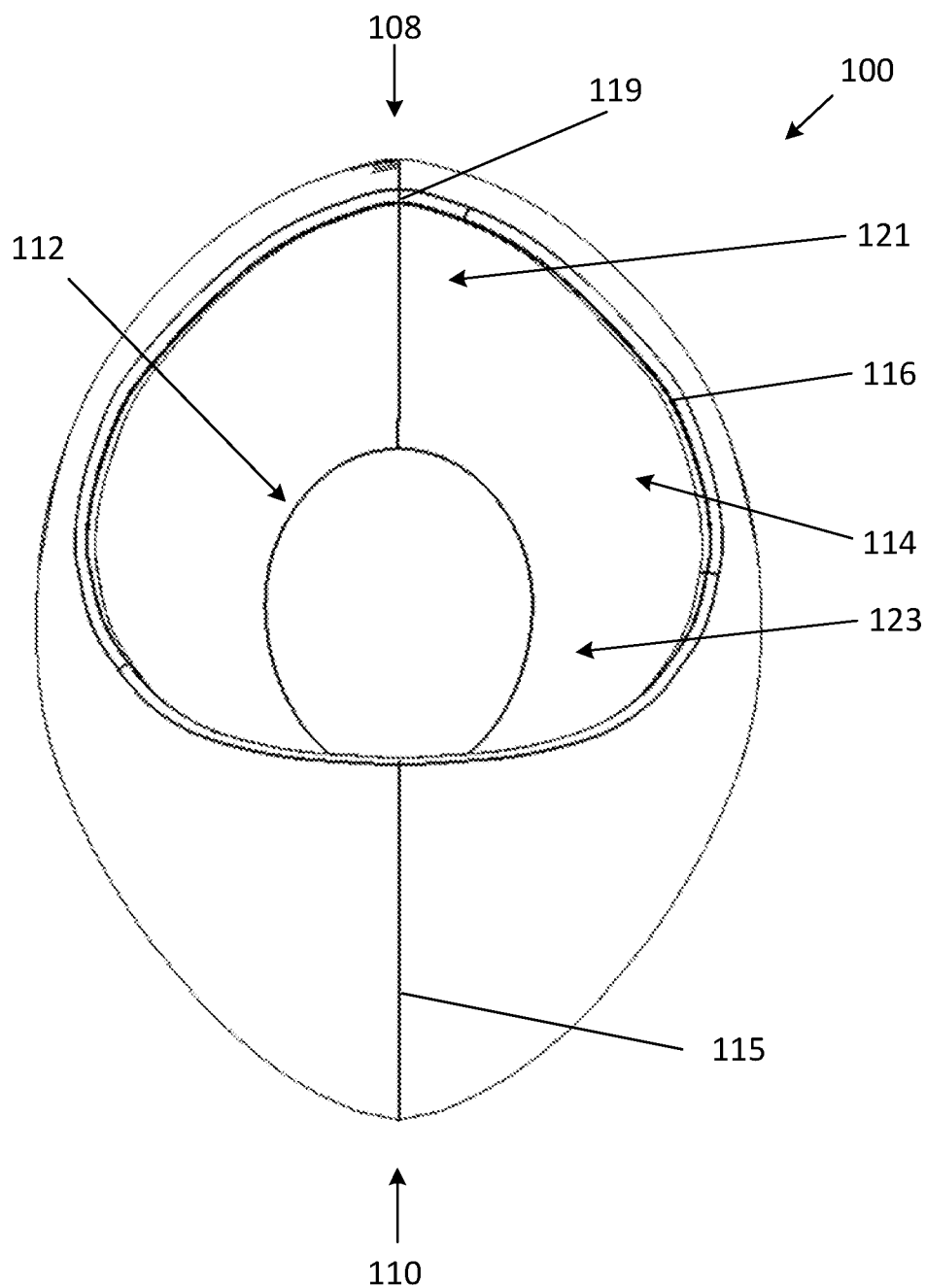
FIG. 2 is a rear view of the apparatus for collecting breast milk shown in FIG. 1.

Referring to FIG. 1, illustrated therein is an apparatus 100 for collecting breast milk. Apparatus 100 has a body 102 having a front side 104, a rear side 106 opposed to the front side 104, a top side 108 and a bottom side 110 opposed to the top side 108. Body 102 defines a cavity 112 therein (see FIG. 2) for collecting breast milk. Cavity 112 is accessible through an opening 114 in the rear side 106 of body 102.

Turning to FIGS. 2 to 7, body 102 can act as both a shield and a receptacle for collecting breast milk. For instance, when the apparatus 100 is placed adjacent to (i.e. spaced from) or against a breast of a user with the opening 114 generally facing the nipple of the breast, the body can act as a shield in that breast milk expressed from the user's breast can be expressed through the opening 114, deflected off of inner wall 124 of body 102 and directed into cavity 112. In some embodiments, milk expressed from the user's breast can be expressed through the opening 114 and directly fall into cavity 112 (e.g. by gravity). Holding the apparatus 100 adjacent to (i.e. spaced from) a breast of a user with the opening 114 generally facing the nipple of the breast can provide for the user to press their hand against the area of the breast immediately surrounding the nipple to manually activate the myoepithelial cells that naturally contract during breastfeeding to encourage the expression of breast milk from the alveoli. Opening may be sized and shaped to redirect and capture expressed milk exiting the user's breast from all anatomically possible angles.

Opening 114 may be positioned upwardly on body 102 (e.g. towards top side 108) to engage with a user's breast. Positioning opening 114 towards top side 108 may provide for breast milk entering cavity 112 through opening 114 to collect in a lower portion 123 of the body 102 (described further below). In some embodiments a center of the opening 114 is vertically offset from a center of the body. Opening 114 can be sized to substantially surround at least a nipple of a user's breast when the body 102 is oriented such that opening 114 faces the user's breast for receiving breast milk expressed therefrom. Opening 114 can generally have any shape. For example, opening 114 may be circular, square, rectangular, triangular, etc.

Body 102 can be formed from a variety of materials including polypropylene, silicone or any other polymeric materials that are flexible, pliable, food grade (e.g. to inhibit contamination of the breast milk) and can be subsequently washed (e.g. with soap and hot water and/or in a dishwasher), reused and sterilizable.

In some embodiments, body 102 may be formed by compression molding. For instance, body 102 may be formed by joining (e.g. combining, or fixing) two halves of body 102 together to form a seam 115. Seam 115 may extend around body 102. For instance, seam 115 may extend from an upper portion 121 of opening 114 around front side 104 of body 102 to bottom portion 123 of opening 114 (see FIGS. 4 and 5). Seam 115 may bisect body 102. In some embodiments, seam 115 may be interrupted by a flattened portion 117 of body 102. In other embodiments, body 102 may also be formed by injection molding.

The embodiment of apparatus 100 shown in FIGS. 1 to 9 is shown with a flattened portion 117 formed on front side 104 of the body 102 to provide for the apparatus 100 to be set down on a flat surface, without tipping or wobbling, while containing milk. However, alternative embodiments could be made without flattened portion 117. Alternatively, flattened portion 117 may be positioned on any of top side 108, bottom side 110 and front side 104. As shown, flattened portion 117 is positioned on front side 104 opposed to opening 114 to provide for apparatus 100 to be set down on a flat surface without spilling any breast milk in cavity 112.

Body 102 can have a lip 116 surrounding opening 114. Lip 116 can be rounded to provide for a soft feel against a user's breast. Opening 114 may be shaped to conform to a natural breast profile of a user. In some embodiments, opening 114 may be shaped to form a tight fitting seal (i.e. sealingly engage) with the breast. In some embodiments, a tight fitting seal may be a vacuum tight seal such that the apparatus 100 can be applied to a breast and remain removably coupled to the breast via a negative pressure in cavity 112. In this manner, the apparatus 100 may be "hands-free" as the apparatus 100 may be retained on the user's breast during the collection of breast milk without the user having to hold or support the apparatus.

In some embodiments, opening 114 may be generally triangular shaped having an apex 119 adjacent to top side 108 of the body 102. Upper portion 121 of opening 114 may be narrower than lower portion 123 (i.e. lower portion 123 may extend laterally from upper portion 121 of opening 114).

Apex 119 of opening 114 may form a spout for pouring milk out of the cavity. Apex 119 may encourage laminar flow of milk poured out of the cavity 112. In some embodiments, apex 119 may intersect with seam 115 joining two halves of the body 102 to form the spout for pouring milk out of the cavity. In some embodiments, the spout may extend or protrude from the opening for pouring milk out of cavity 112.

Figure 3:
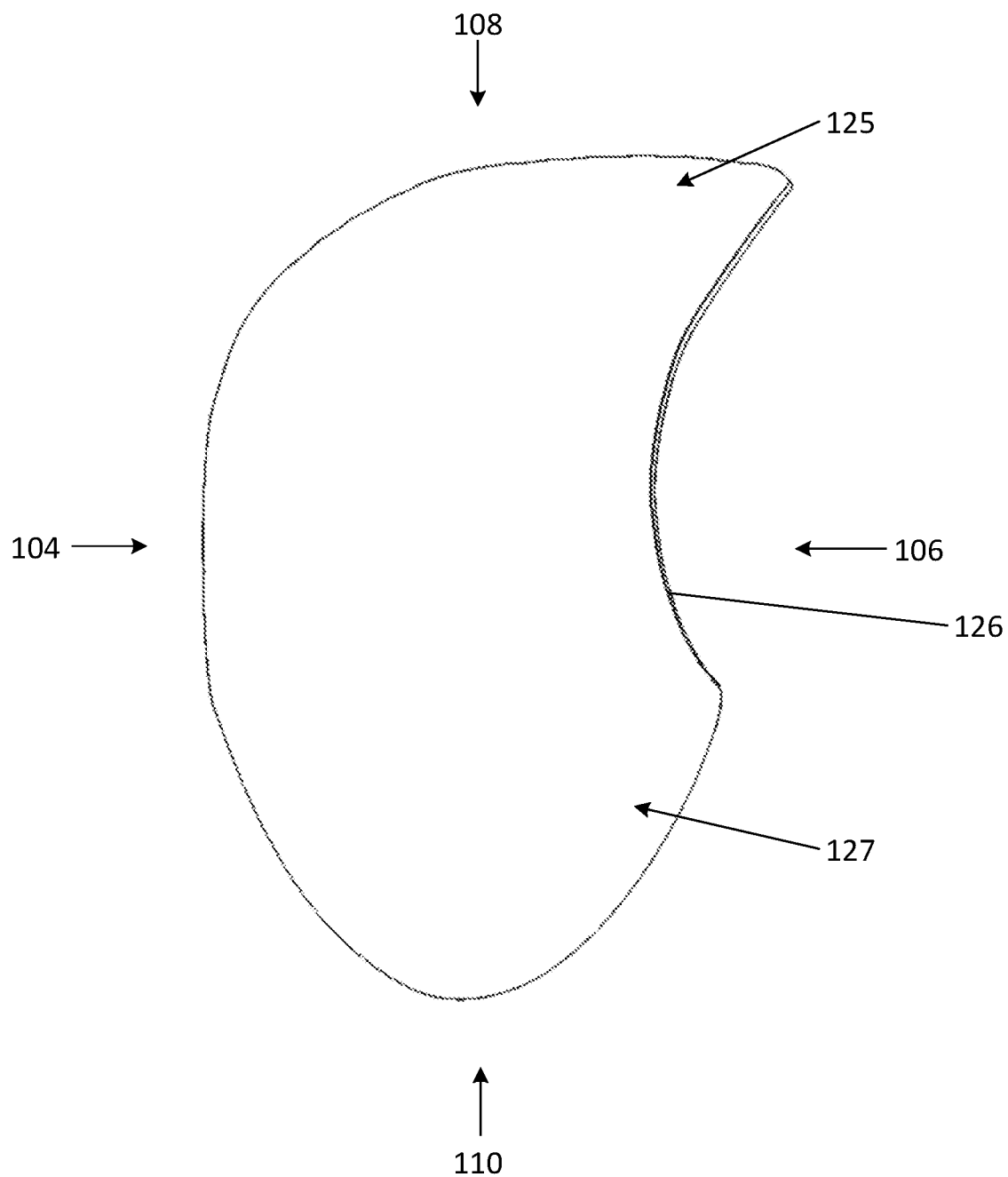
FIG. 3 is a right side view of the apparatus for collecting breast milk shown in FIG. 1.
Figure 4:
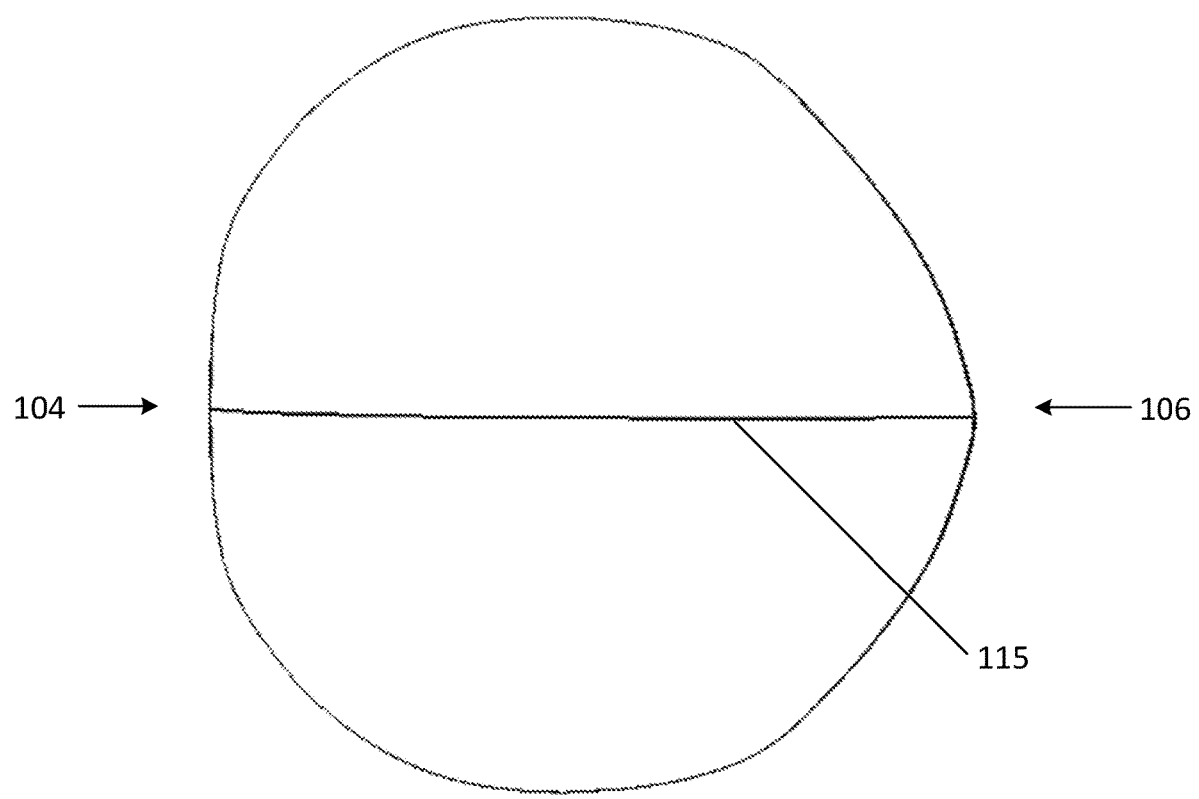
FIG. 4 is a top view of the apparatus for collecting breast milk shown in FIG. 1.
Figure 5:
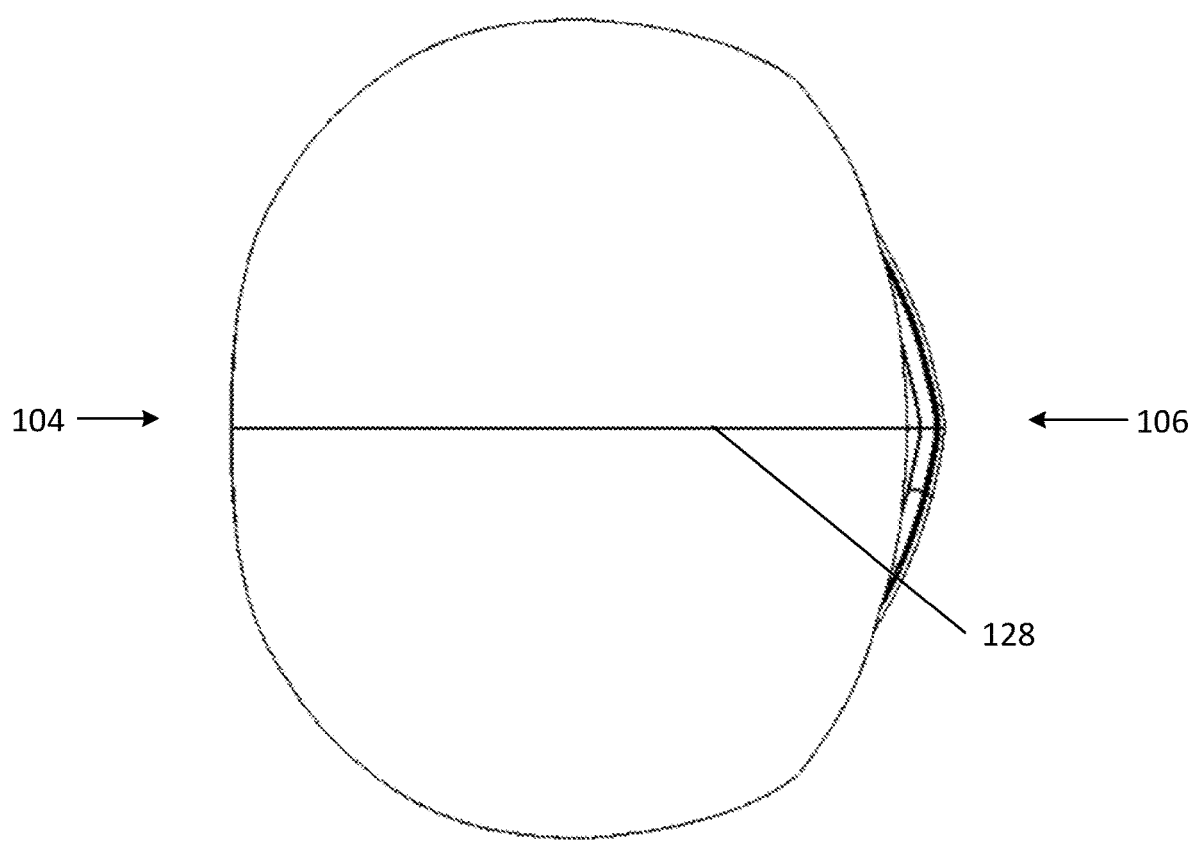
FIG. 5 is a bottom view of the apparatus for collecting breast milk shown in FIG. 1.
Figure 6:
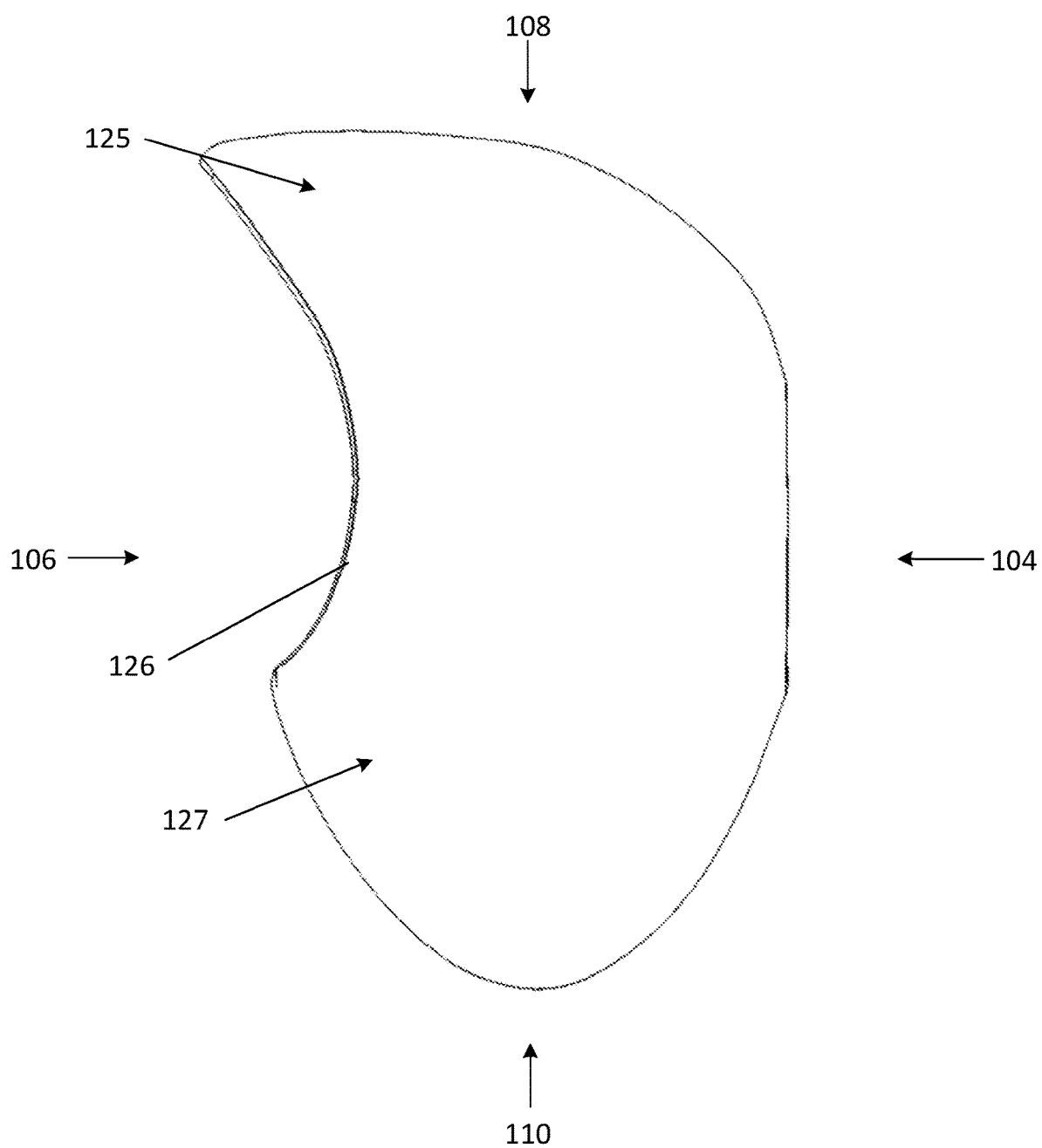
FIG. 6 is a left side view of the apparatus for collecting breast milk shown in FIG. 1.
Figure 7:
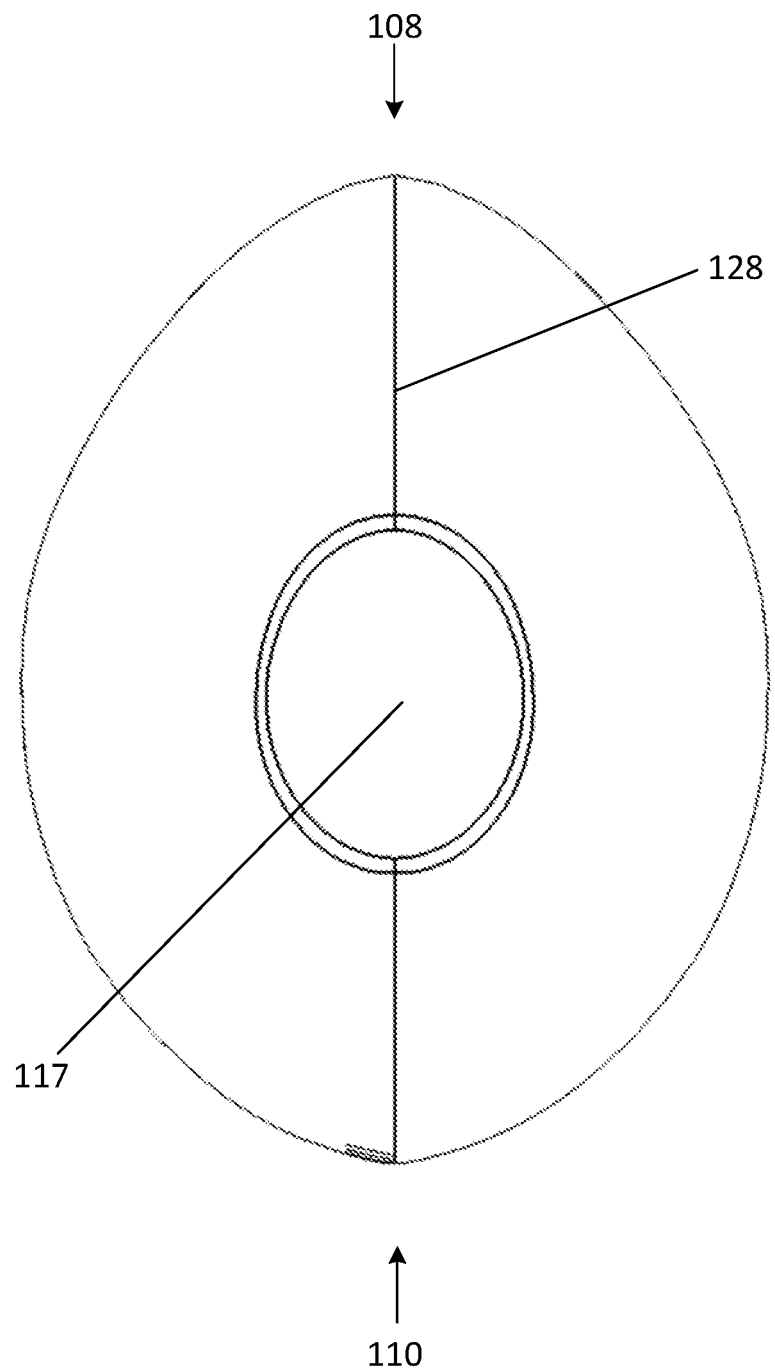
FIG. 7 is a front view of the apparatus for collecting breast milk shown in FIG. 1.
Figure 8:
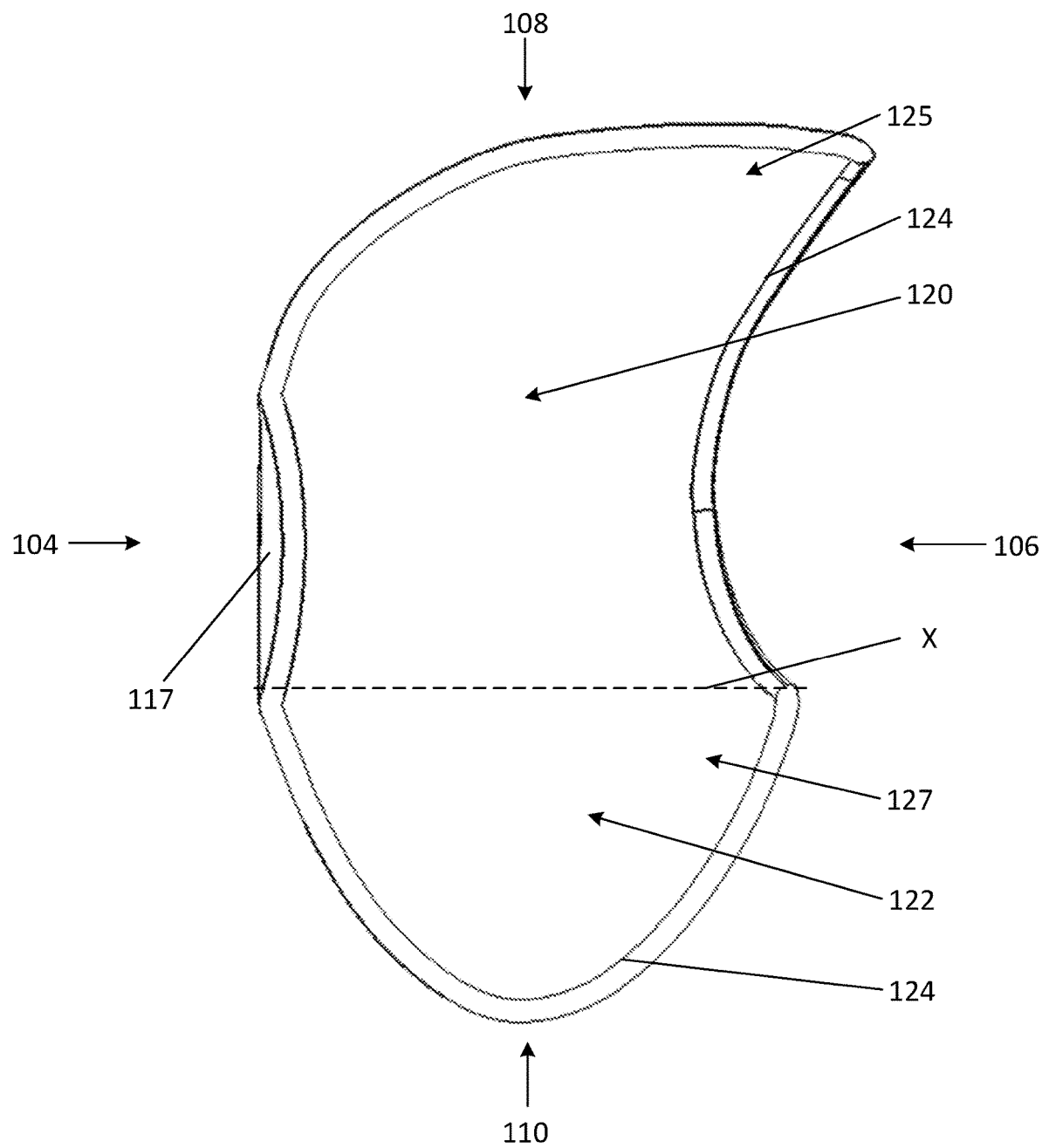
FIG. 8 is a cross-section view from side to side of the apparatus for collecting breast milk shown in FIG. 1.
Figure 9:
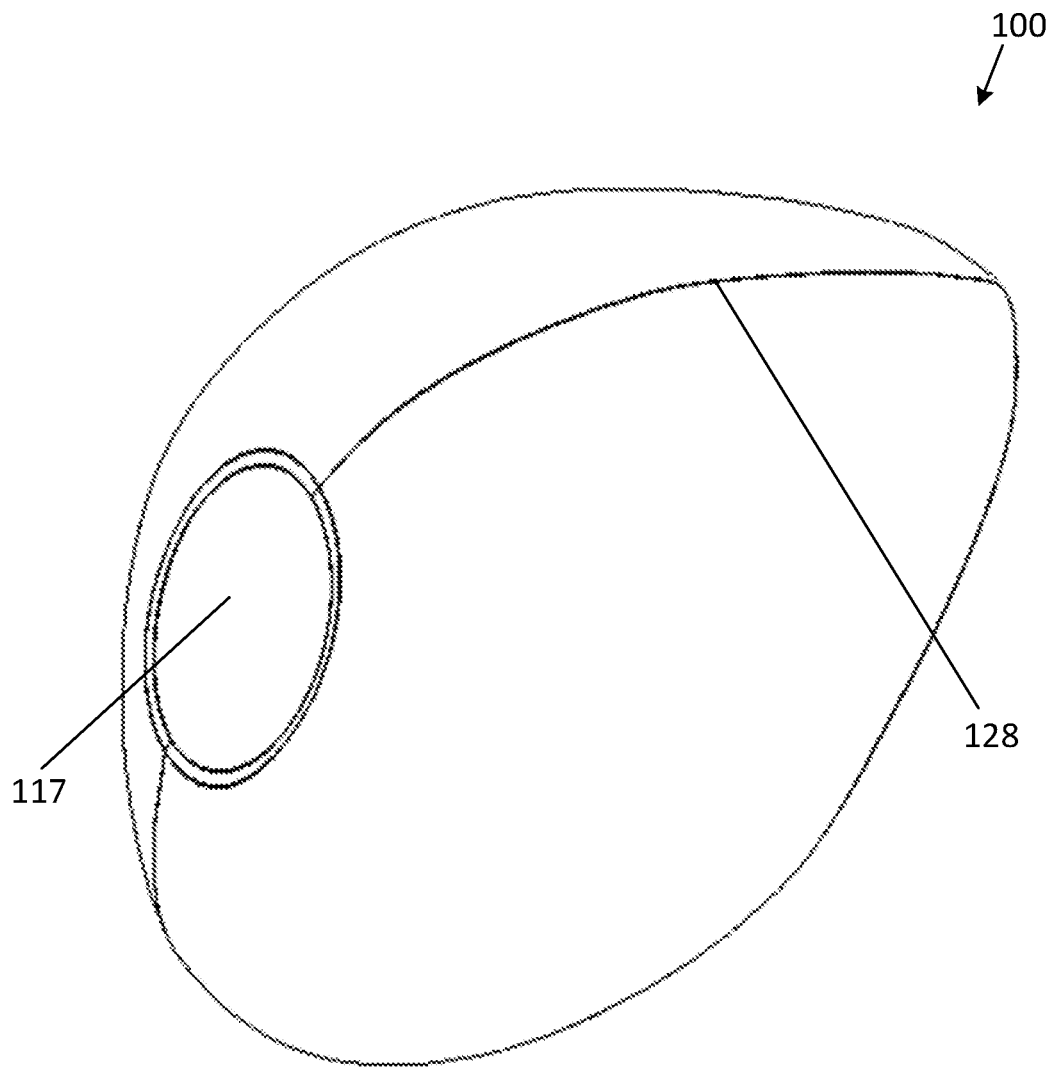
FIG. 9 is a front perspective view from above of the apparatus for collecting breast milk shown in FIG. 1.
Figure 10:
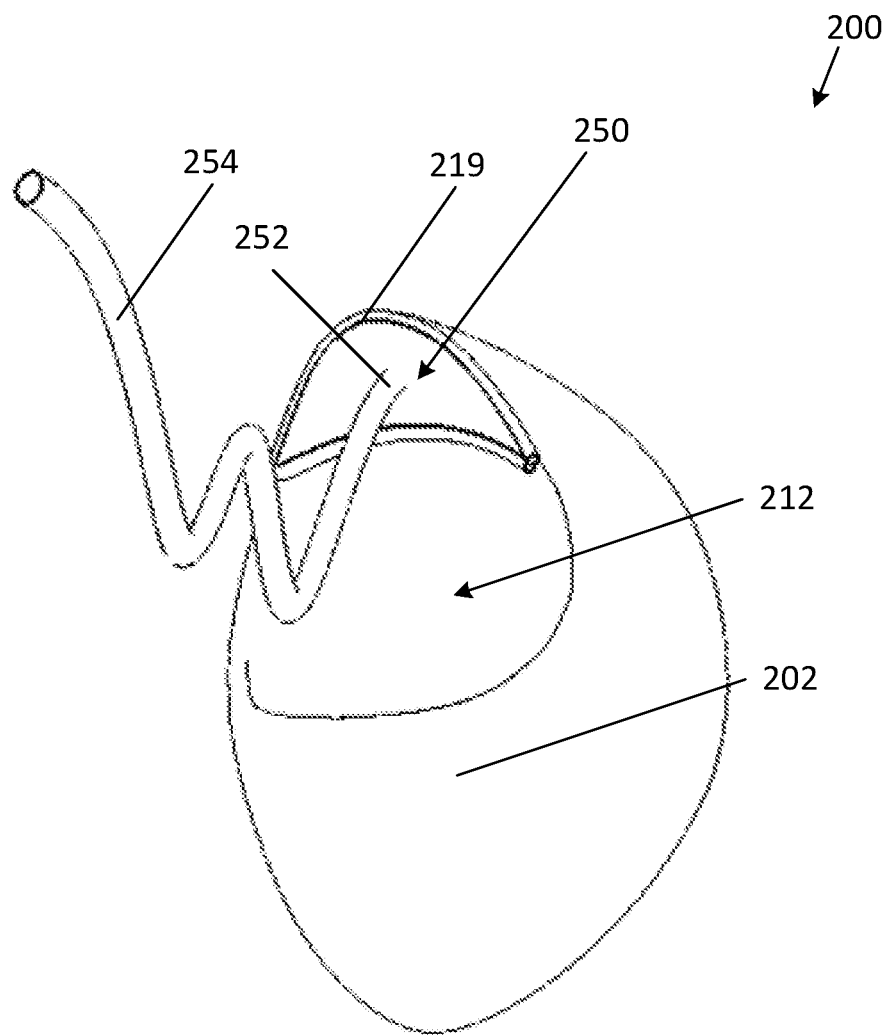
FIG. 10 is a rear perspective view of an apparatus for collecting breast milk, according to another embodiment.
Figure 11:
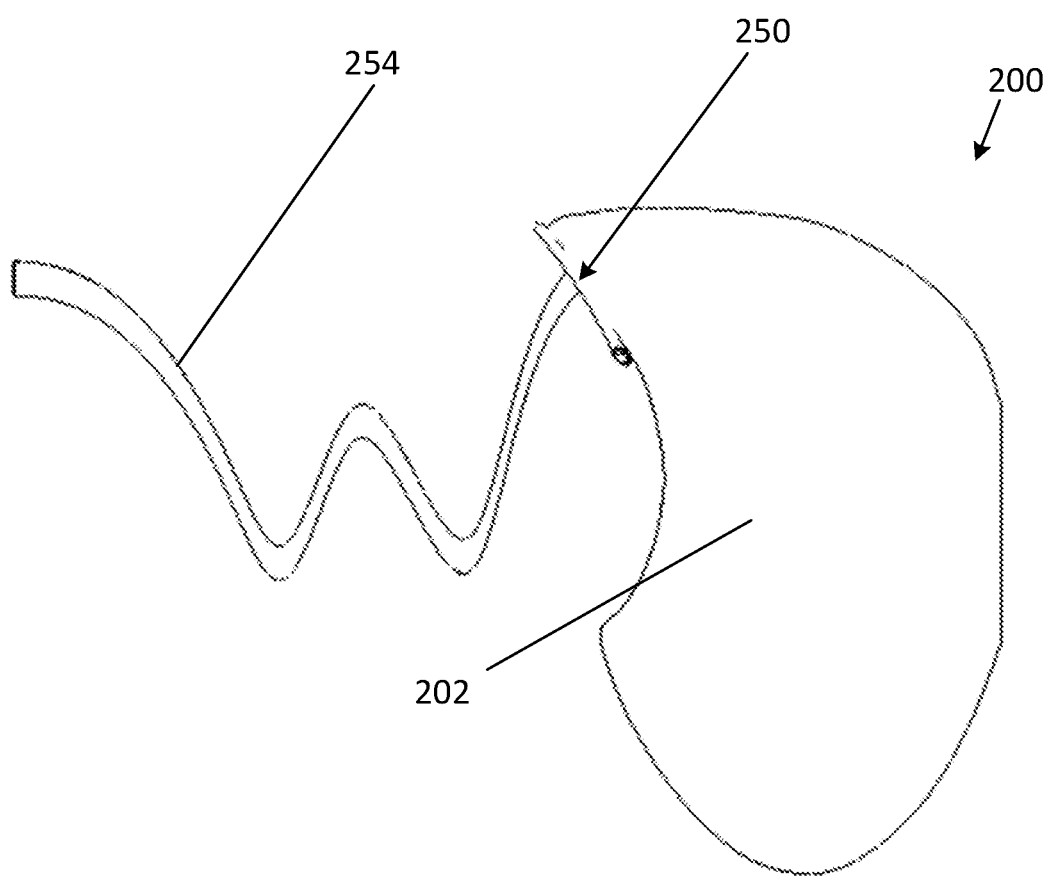
FIG. 11 is a side view of the apparatus for collecting breast milk of FIG. 10.
Figure 12:
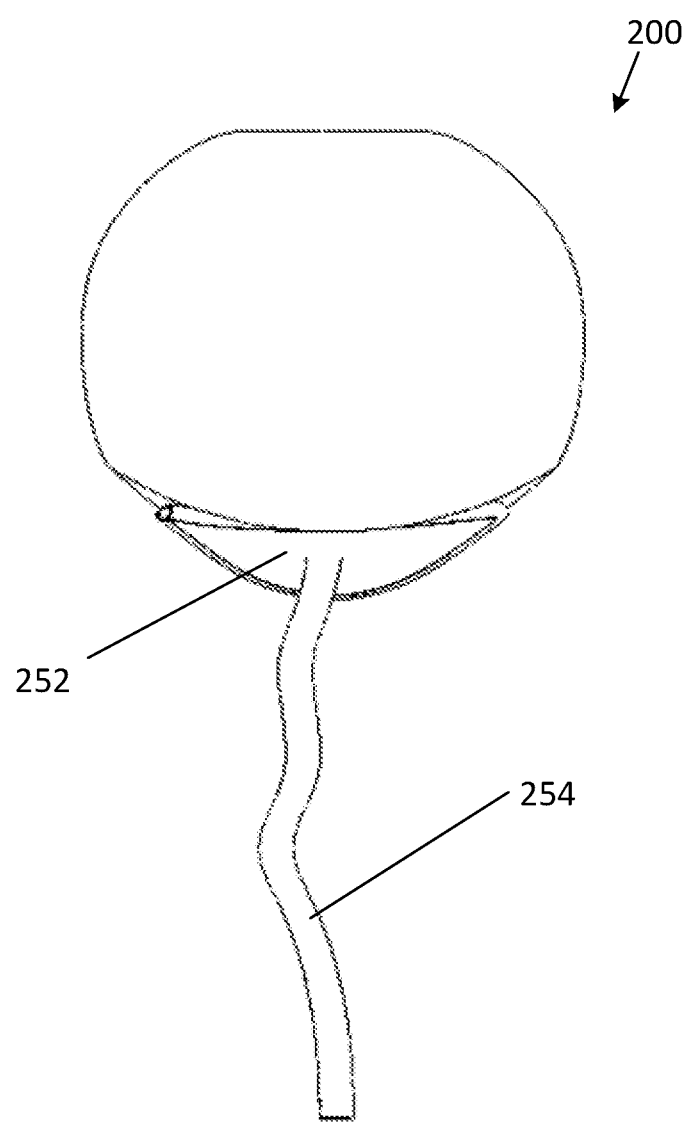
FIG. 12 is a bottom view of the apparatus for collecting breast milk of FIG. 10.
Figure 13:
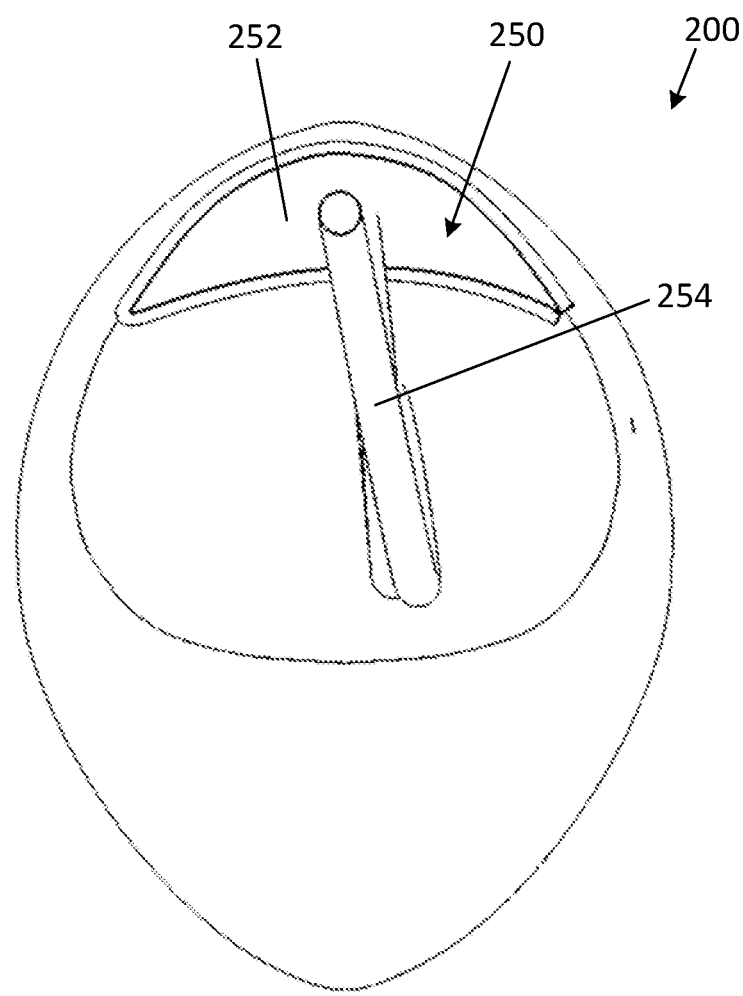
FIG. 13 is a rear view of the apparatus for collecting breast milk of FIG. 10.

Opening 114 may be shaped to provide for sealing engagement of a user's breast while collecting expressed or leaking milk from the breast. For instance, as shown in FIGS. 3, 6 and 8, an upper extending portion 125 of body 102 may extend rearwardly towards rear side 106 define the upper portion 121 of opening 114. Upper portion 121 of opening 114 may conform to a natural slope of an upper portion of a user's breast (e.g. a portion of the breast upwards from the nipple). Upper portion 121 of opening 114 may form part of a spout for pouring milk out of the cavity. Similarly, a lower extending portion 127 of body 102 may also extend rearwardly towards rear side 106 to define the lower portion 123 of opening 114. Lower portion 123 of opening 114 may conform to a natural slope of a lower portion of a user's breast (e.g. a portion of the breast below the nipple).

Opening 114 may also be shaped to provide for close engagement of apparatus 100 to the breast of the user. For instance, opening 114 may have a concave shape to provide for the nipple of the user to enter the cavity 112 without the side portions 126 of the opening contacting the user's breast. This may provide for a user to place their hands against the breast immediately adjacent to the nipple to manually express milk from the breast while their nipple protrudes into cavity 112. This concave shape of opening 114 may provide for efficient collection of milk as expressed milk can be retained in cavity 112. The concave shape of opening 114 may also provide for a user of apparatus 100 to maintain a good posture during use as the user will not have to lean over the apparatus 100 for the apparatus 100 to collect the breast milk expressed from their breast.

In some embodiments, upper extending portion 125 of body 102 may rearwardly extend towards rear side 106 a greater distance than lower extending portion 127 of body 102. Upper extending portion 125 of body 102 may form a part of a spout for pouring breast milk from the cavity 112. In some embodiments, the spout is shaped to conform to an infant's mouth or a storage container.

Cavity 112 has an upper region 120 and a lower region 122 (see FIG. 8). Upper region 120 is bounded by an inner wall 124 of the body 102 and the opening 114. When apparatus 100 is being used to collect breast milk, upper region 120 can either receive at least a portion of a user's breast or be facing (and spaced from) at least a portion of the using breast. For instance, upper region 120 may receive or face a portion of the user's breast having a nipple for the user to express milk from the breast and the nipple into cavity 112 of apparatus 100. In some embodiments, the inner wall 124 of the lower region 122 is tapered (i.e. extends) outwardly as it extends upwardly from the lower region 122 towards the upper region 120. In these embodiments, the tapered wall 124 can provide for the lower region 122 to fill up quickly even when the expressed milk volume is low (e.g. to provide positive feedback to the user) and to accommodate milk volumes in a range of about 50 mL to about 150 mL.

Lower region 122 is generally oriented downward from opening 114 when the apparatus is being used to collect breast milk. In this manner, lower region 122 forms a reservoir for collecting breast milk expressed from a user. Lower region 122 is generally bounded by inner wall 124 of body 102 and is considered to be a portion of the body 102 below a lowest point of opening 114 when the body 102 is oriented for use (see, for example, boundary line X on FIG. 8). In this manner, a capacity of lower region 122 is generally measured as the volume of the portion of the body 102 below a lowest point of opening 114 when the body 102 is oriented for use. In some embodiments, the lower region 122 of the cavity 112 may be sized to have a capacity in a range of about 50 mL to 150 mL of breast milk. In some embodiments, the lower region 122 of the cavity 112 may be sized to have a capacity in a range of about 50 mL to 100 mL of breast milk. In some embodiments, the lower region 122 of the cavity 112 may have a capacity of about 75 mL.

Body 102 can be formed from a variety of materials including polypropylene, silicone or any other polymeric materials that are flexible, pliable, food grade (e.g. to inhibit contamination of the breast milk) and can be subsequently washed (e.g. with soap and hot water and/or in a dishwasher), reused and sterilizable.

Referring now to FIGS. 10 to 13, illustrated therein is another embodiment of an apparatus for collecting milk. Apparatus 200 includes a suction generating device 250 for generating a negative pressure in cavity 212 of body 202 when apparatus 200 is pressed against a breast of a user. The negative pressure may encourage the breast to express milk. The negative pressure may also encourage the apparatus 200 to sealingly engage the breast of the user and may provide for the apparatus 200 to be used in a hands-free manner (e.g. apparatus 200 may be retained on the breast of the user due to the negative pressure in the cavity 212 for the collection of expressed or leaking milk).

The suction generating device 250 may be coupled to the body 202. For instance the suction generating device 250 may be coupled to the body 202 adjacent to the opening 214.

Suction generating device 250 is positioned in an upper portion 221 of the opening 214. In this example embodiment, opening 214 may have a smaller area when compared to the area of opening 114 of apparatus 100. Suction generating device 250 may also be positioned in the apex 219 of the opening 214.

In some embodiments, body 102 may define an aperture (not shown) for coupling to suction generating device 250 and for suction generating device 250 to modulate a negative pressure in cavity 212.

Suction generating device 250 may include a valve 252 for sealing the cavity 212 when the apparatus 200 is against the breast of a user. Valve 252 may be a gate valve, a plug valve, a butterfly valve, a globe valve, a pinch valve, a disc check valve or the like.

Suction generating device 250 may also include a tube 254 for generating the negative pressure in the cavity 212. For instance, the user may use tube 254 to manually remove air from cavity 212 when the apparatus 200 is placed against the user's breast.

Further, a manual pump (e.g. plunger or the like) or an electric pump may be coupled to hose 254 to modulated a negative pressure in cavity 212.

While the above description provides examples of one or more apparatus, methods, or systems, it will be appreciated that other apparatus, methods, or systems may be within the scope of the claims as interpreted by one of skill in the art.

What is claimed is:

1. A single-piece apparatus for collecting breast milk from a user, the single-piece apparatus comprising:
    a body formed from a flexible polymeric material, the body defining a cavity therein, the cavity having an upper region for receiving a portion of the user's breast and a lower region below the upper region forming a reservoir for collecting the breast milk, the body having:
        a front side and a rear side opposed to the front side; and
        a lip on the rear side of the body forming a perimeter around an opening leading into the upper region of the cavity, at least a portion of the lip curving inwardly from the rear side of the body in a direction towards the front side of the body.

2. The apparatus of claim 1, wherein the lip includes a top portion, a bottom portion and opposed side portions, each of the opposed side portions extending between the top portion and the bottom portion, at least a portion of each of the side portions of the lip curving inwardly from the rear side of the body towards the front side of the body.

3. The apparatus of claim 1, wherein the reservoir is lower than a lowest point of the lip and the portion of the lip that curves inwardly is above the reservoir.

4. The apparatus of claim 1, wherein an upper portion of the opening is narrower than a lower portion.

5. The apparatus of claim 1, wherein the opening includes a spout positioned adjacent to a top side of the body for pouring milk out of the cavity through the opening.

6. The apparatus of claim 5, wherein the spout is shaped to conform to an infant's mouth or a storage container.

7. The apparatus of claim 5, wherein the spout extends rearwardly from the body relative to a lower portion of the opening.

8. The apparatus of claim 1, wherein a center of the opening is vertically offset from a center of the body.

9. The apparatus of claim 1, wherein a center of the opening is horizontally aligned with a center of the body.

10. The apparatus of claim 1, wherein the lip is non-planar.

11. The apparatus of claim 1, wherein the cavity is sized to retain a volume of breast milk in a range of about 50 mL to 150 mL when the body is upright.

12. The apparatus of claim 1, wherein the body includes a flattened portion to provide for the single-piece apparatus to rest on a flat surface without falling over.

13. The apparatus of claim 12, wherein the flattened portion is on one of a top, a bottom and the front side of the body.

14. The apparatus of claim 12, wherein the flattened portion is opposed to the opening.

15. The apparatus of claim 1, wherein an inner wall of the body is tapered outwardly from a lower region of the body to an upper region of the body.

* * * * *